(12) United States Patent
Hillman et al.

(10) Patent No.: US 10,129,508 B1
(45) Date of Patent: Nov. 13, 2018

(54) PROPERTY INSPECTION DEVICES, METHODS, AND SYSTEMS

(71) Applicant: UNITED SERVICES AUTOMOBILE ASSOCIATION (USAA), San Antonio, TX (US)

(72) Inventors: James P. Hillman, Kennewick, WA (US); Cynthia D. Blasing, Hondo, TX (US); Damien J. Brunet, Schertz, TX (US); Dan D. Cable, Garden Ridge, TX (US); Adolfo J. Fernandez, San Antonio, TX (US); Jeffrey A. Kreth, San Antonio, TX (US); Shane C. Osborne, Marion, TX (US); Robert A. Pacheco, San Antonio, TX (US); Renee A. Sokolowski, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 135 days.

(21) Appl. No.: 15/091,365

(22) Filed: Apr. 5, 2016

Related U.S. Application Data

(63) Continuation-in-part of application No. 14/505,769, filed on Oct. 3, 2014, which is a continuation-in-part of application No. 13/781,389, filed on Feb. 28, 2013, now Pat. No. 9,706,173, which is a continuation-in-part of application No. 13/298,083, filed on Nov. 16, 2011, now Pat. No. 9,706,172.

(60) Provisional application No. 61/532,470, filed on Sep. 8, 2011.

(51) Int. Cl.
  H04N 7/18        (2006.01)
  G06Q 40/08       (2012.01)
  G06Q 50/16       (2012.01)

(52) U.S. Cl.
  CPC ............. H04N 7/185 (2013.01); G06Q 40/08 (2013.01); G06Q 50/16 (2013.01)

(58) Field of Classification Search
  CPC ........... H04N 7/18; H04N 7/183; G03B 17/56
  See application file for complete search history.

(56) References Cited

U.S. PATENT DOCUMENTS

| 4,027,528 | A |   | 6/1977 | Tyree |
| 4,312,162 | A |   | 1/1982 | Medney |
| 5,065,249 | A |   | 11/1991 | Horn et al. |
| 5,399,009 | A |   | 3/1995 | Hiner |
| 5,686,652 | A | * | 11/1997 | Pfund ..................... G01M 7/08 73/12.04 |
| 6,056,450 | A |   | 5/2000 | Walling |
| 7,869,944 | B2 |   | 1/2011 | Deaton et al. |

(Continued)

OTHER PUBLICATIONS

"Infrared Camera Rentals" Sep. 29, 2011, 3 pages, Retrieved from Internet <http://www.atlas-inspection.com/infrared-camera-rentals.html>.

(Continued)

Primary Examiner — Anner N Holder
(74) Attorney, Agent, or Firm — Baker Hostetler LLP

(57) ABSTRACT

The present disclosure describes structural inspection devices, methods, and systems. One inspection device includes a pole, a sensor coupled to an end of the pole and configured to capture a multispectral image of a roof, and a number of attachments coupled to the pole and configured to stabilize the pole on or within the structure.

20 Claims, 7 Drawing Sheets

(56) References Cited

U.S. PATENT DOCUMENTS

| | | | |
|---|---|---|---|
| 8,346,578 B1* | 1/2013 | Hopkins, III | G06Q 40/00 382/100 |
| 8,634,771 B2 | 1/2014 | Hassan et al. | |
| 2002/0097321 A1 | 7/2002 | McBride | |
| 2004/0136388 A1 | 7/2004 | Schaff | |
| 2006/0158549 A1 | 7/2006 | Digweed et al. | |
| 2006/0235611 A1* | 10/2006 | Deaton | G01C 15/00 701/491 |
| 2007/0053680 A1 | 3/2007 | Fromm | |
| 2007/0096928 A1* | 5/2007 | Lee | A01M 1/026 340/573.2 |
| 2007/0146700 A1* | 6/2007 | Kowarz | G01J 3/02 356/310 |
| 2008/0162380 A1 | 7/2008 | Suga et al. | |
| 2008/0262789 A1* | 10/2008 | Pershing | G06Q 10/00 702/156 |
| 2009/0216552 A1 | 8/2009 | Watrous | |
| 2009/0265193 A1 | 10/2009 | Collins et al. | |
| 2010/0140461 A1* | 6/2010 | Sprigle | G01J 3/2823 250/226 |
| 2010/0202769 A1* | 8/2010 | Polster | G03B 17/38 396/420 |
| 2012/0076485 A1 | 3/2012 | Zwahr | |
| 2012/0211978 A1 | 8/2012 | Gardiner | |
| 2012/0322368 A1 | 12/2012 | Desai et al. | |

OTHER PUBLICATIONS

"Remote Visual Inspection—Overview" Sep. 29, 2011, 1 page, Retrieved from internet <http://www.ashtead-technology.com/us/RemoteVisual/Content/Overview.html>.

Rovver 225 Sep. 29, 2011, 6 pages, Retrieved from internet < http://www.ge-mcs.com/en/remote-visual-inspection/robotic-crawlers/rovver-225 .html>.

"Telescopic Inspection Camera" Sep. 29, 2011, 2 pages, Retrieved from internet <http://www.ukinspectioncamera.co.uk/acatalog/Telescopic_Camera_Pixie_Click.html>.

* cited by examiner

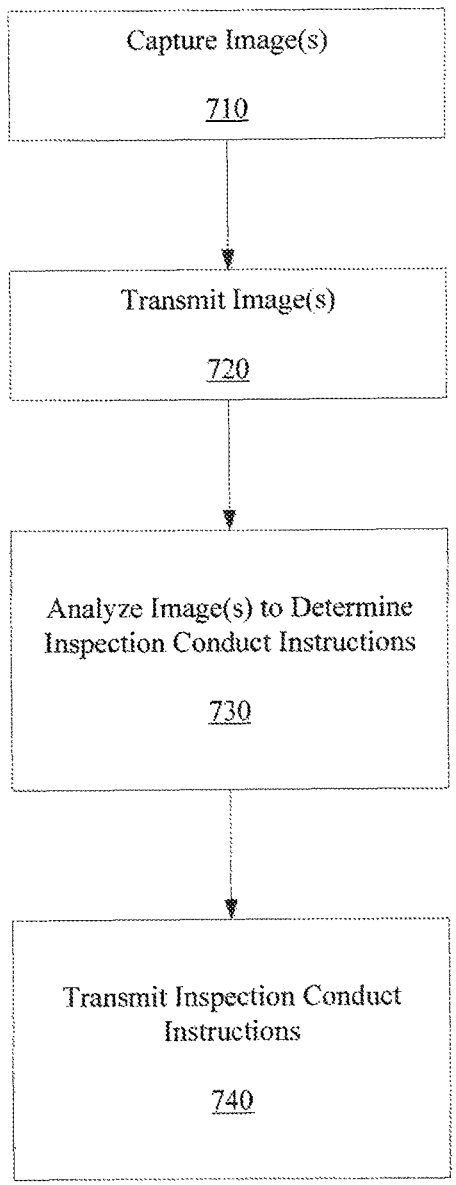
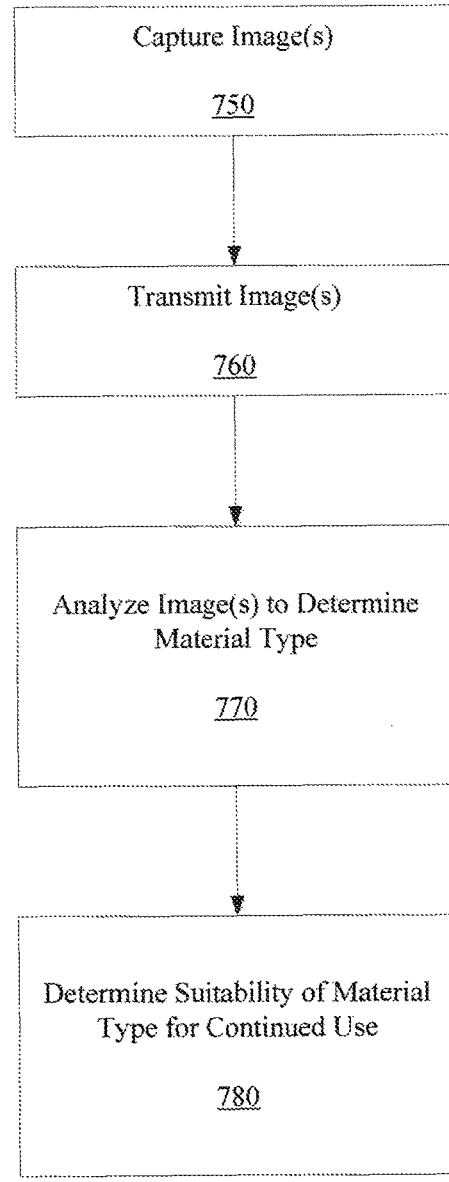
FIG. 7a
FIG. 7b

PROPERTY INSPECTION DEVICES, METHODS, AND SYSTEMS

CROSS-REFERENCE TO RELATED APPLICATIONS

This application is a continuation in part of U.S. application Ser. No. 14/505,769, filed Oct. 3, 2014, which a continuation in part of U.S. application Ser. No. 13/781,389, filed Feb. 28, 2013, which is a continuation in part of U.S. application Ser. No. 13/298,083, filed Nov. 16, 2011, which claims the benefit of U.S. Provisional Application No. 61/532,470, filed Sep. 8, 2011, the entire specifications of which are incorporated herein by reference.

FIELD OF THE INVENTION

The disclosed embodiments generally relate to property inspection systems, and more particularly, the use of remotely located, and controlled, electronic inspection devices for conducting property inspections.

BACKGROUND OF THE INVENTION

In some circumstances, an insurance company may need to inspect the roof, walls, windows, or any other elevated surface not accessible from the ground of a building (e.g., a house and/or dwelling) covered by an insurance policy issued by the insurance company. For example, if the roof of a building covered by an insurance policy is damaged due to, for instance, a storm, wind, hail, falling tree(s), water, and/or fire, among other causes of damage, the insurance company may need to inspect a difficult to access regions (e.g., a damaged roof, underneath a vehicle, behind vehicle fender wells, and other location not readily accessible by an inspector) as part of a claims process. For instance, the insurance company may need to assess the condition of the roof (e.g., the extent and/or amount of the damage to the roof) in order to determine whether a loss exists and/or estimate the cost of repairing the damage.

In some previous roof inspection approaches, a human representative (e.g., a claims adjuster) of the insurance company may need to physically climb on to the roof (e.g., using a ladder) and/or walk around on the roof in order to inspect the roof. However, such a roof inspection method can be dangerous for the claims adjuster. Further, such a roof inspection method can be costly and/or time consuming for the insurance company.

SUMMARY OF THE INVENTION

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

To achieve these and other advantages and in accordance with the purpose of the illustrated embodiments, in one aspect, a roof inspection system and method is described in which in one illustrated embodiment provided is system including a device consisting of an extendable pole; an adjustable sensor mount coupled to an end of the extendable pole; a releasable sensor device (e.g., a multispectral sensor device) coupled to the adjustable sensor mount; an extendable bipod attachment coupled to the extendable pole and configured to stabilize the extendable pole on or within a structure. A remote device is provided which is configured to instruct the releasable sensor device to capture a multispectral image of the structure and send the captured multispectral image to the remote device wherein the remote device electronically provides advanced processing and analysis and transmits the captured multispectral image. A computer server is located remotely from the mobile device configured to electronically receive the captured multispectral image from the remote device and provide advanced analysis of the captured multispectral image with regards to facilitating an inspection process.

BRIEF DESCRIPTION OF THE DRAWINGS

FIGS. 7a and 7b illustrate methods of operation for the inspection system and claim processing system of FIGS. 5 and 6.

DETAILED DESCRIPTION

Figure 1A:
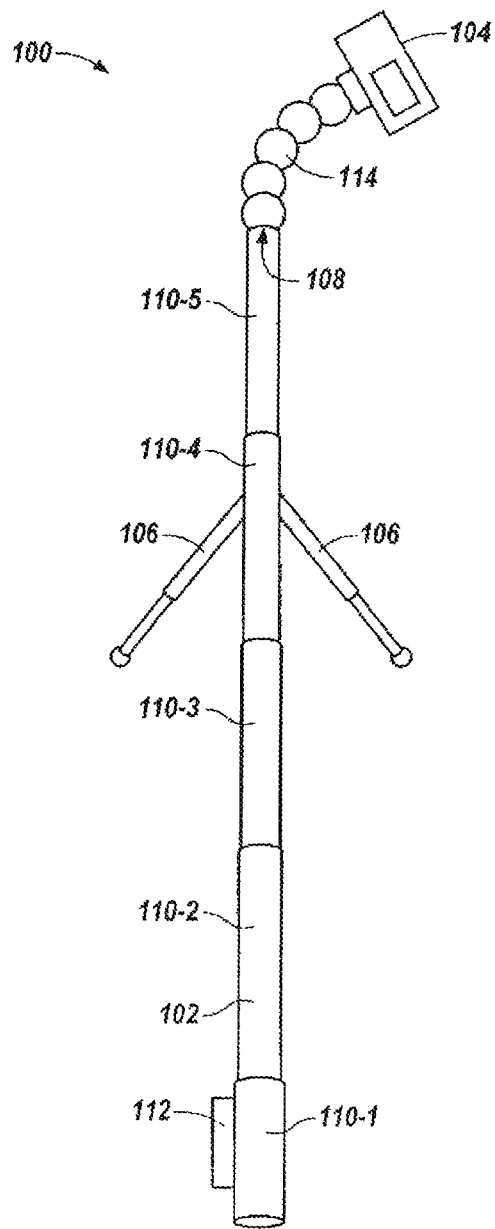
FIGS. 1A and 1B illustrate a system for inspecting a roof in accordance with one or more embodiments of the present disclosure.

The present disclosure describes roof inspection devices, methods, and systems. One or more embodiments include a pole, a camera, and/or multispectral sensor, coupled to an end of the pole and configured to capture imaging data from a structure, and a number of attachments coupled to the pole and configured to stabilize the pole on or within the structure, such as on a roof, in an attic, crawlspace, and/or on an elevated or subterranean surface.

Inspection devices, methods, and/or systems in accordance with the present disclosure can be safer than previous roof inspection approaches (e.g. inspection approaches in which a person physically climbs on to the roof, climbs in an attic, and/or crawls into a crawlspace). Further, inspection devices, methods, and/or systems in accordance with the present disclosure can be safer, less costly and/or less time consuming than previous roof inspection approaches.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 106 may reference element "06" in FIG. 1A and/or FIG. 113, and a similar element may be referenced as 206 in FIG. 2.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense.

As used herein, "a" or "a number of something can refer to one or more such things. For example, "a number of attachments" can refer to one or more attachments.

Figure 1B:
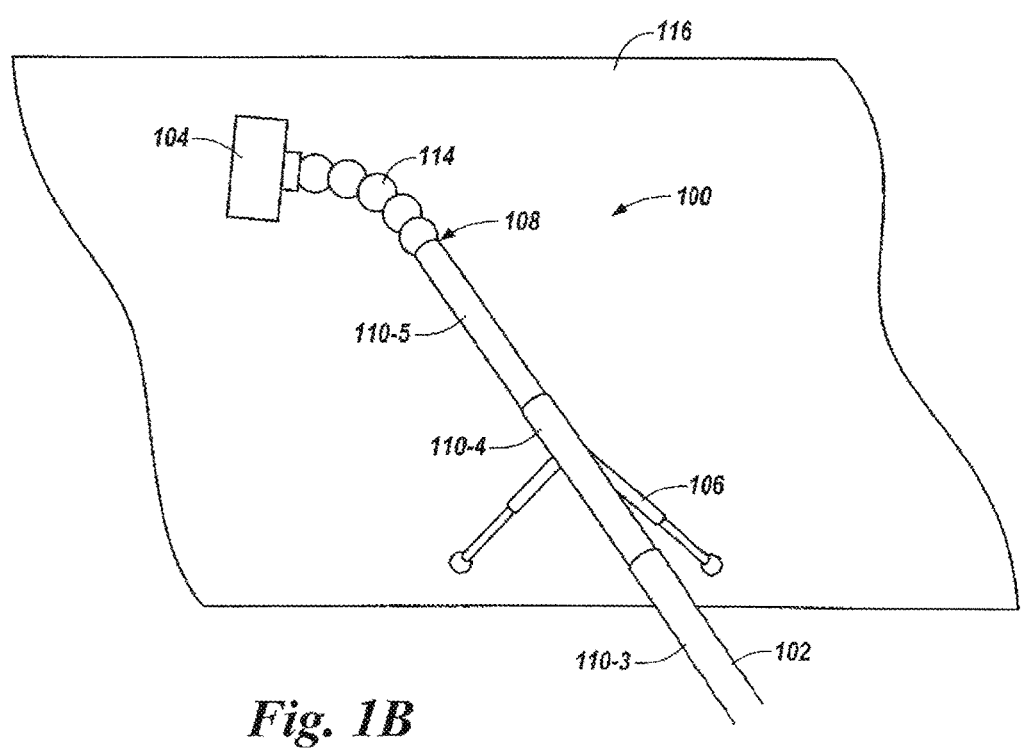

FIG. 1A illustrates a system 100 for inspecting a structure, such as a roof in accordance with one or more embodiments of the present disclosure. FIG. 1B illustrates a portion of the roof inspection system 100 while roof inspection system 100 is in use on (e.g., is being used to inspect) a roof 116. Roof 116 can be, for example, the roof of a building (e.g., a house and/or dwelling) covered by an insurance policy issued by an insurance company. Additionally and/or alternatively, roof 116 can be and/or include any elevated surface that is not accessible from the ground, such as, for instance, a wall(s) or window(s). It is however to be understood the present invention is not to be understood to be limited to a roof inspection as it may encompass inspection of any portion of a structure (e.g., building, vehicle and the like) susceptible to inspection by the present invention inspection system described herein. For ease of description purposes, reference is herein made regarding to inspection of a roof, however, the present invention is not to be understood to be limited to a roof inspection.

As shown in FIGS. 1A and 1B, roof inspection system 100 includes a pole 102. Pole 102 can be, for example, an extendable pole having a number of extendable sections (e.g., segments). For instance, in the embodiments illustrated in FIGS. 1A and 1B, pole 102 includes five extendable sections (e.g., sections 110-1, 110-2, 110-3, 110-4, and 110-5). However, embodiments of the present disclosure are not limited to a particular number of extendable sections for pole 102. In some embodiments, the last section of pole 102 (e.g., section 110-5) can be releasable (e.g., detachable and/or removable) from the rest of the pole (e.g., from the other sections of the pole). Such embodiments would allow for attachment of a sensor to a flying device, floating device, digging device, climbing device, or crawling device that can position the sensor to collect data relevant and necessary to complete an inspection. This may include fiber optic adaptations. A fiber optic adaptation would allow a visual sensor to be extended from pole 102 or a sensor attached thereto rather than extending a sensor by itself. For multi-spectral sensors, similarly accommodating media would be attached to position the sensor to observe input for the purpose of collecting data. An example would include, but not be limited to, a steel rod adapted to a stethoscope to listen for termites.

Pole 102 (e.g., one or more sections of pole 102) can be extended (e.g., partially or fully extended) while roof inspection system 100 is being used to inspect a roof (e.g., roof 116), as illustrated in FIG. 1B. For example, in the embodiments illustrated in FIGS. 1A and 1B, pole 102 is in a fully extended position (e.g., all sections of pole 102 are extended). Pole 102 can be retracted (e.g., not extended) when roof inspection system 100 is not in use. For example, pole 102 can be retracted while roof inspection system 100 is being stored and/or transported.

In some embodiments, pole 102 can be a non-conductive pole. For example, pole 102 can include a non-conductive (e.g., insulator) material such as, for instance, a non-metal material. For instance, pole 102 can be a carbon fiber pole (e.g., include a carbon fiber material). As an additional example, an insulator material, such as, for instance, a fiberglass material, can be wrapped around a portion or all of pole 102.

As shown in FIGS. 1A and 1B, roof inspection system 100 includes an adjustable sensor device mount 114 coupled to an end 108 (e.g., the top) of pole 102. End 108 can be, for instance, a part of (e.g., an end of) the last section of pole 102 (e.g., section 110-5), as illustrated in FIGS. 1A and 1B.

As shown in FIGS. 1A and 1B, adjustable sensor mount 114 (e.g., the position of adjustable mount 114) can be adjusted (e.g., moved and/or bent) with respect to pole 102. Accordingly, adjustable mount 114 can provide flexibility for a data sensing device camera (e.g., a sensor device 104) mounted therein, while at the same time keeping the camera stable while it is in use (e.g., while it is capturing images of roof 116). For instance, a camera mounted in adjustable sensor device mount 114 can capture different images of roof 116 (e.g., images of different portions of roof 116) without moving pole 102 (e.g., while pole 102 remains in the same position on roof 116). Adjustable sensor device mount 114 will be further described herein (e.g., in connection with FIG. 3). It is to be appreciated, for ease of description purposes, reference is herein made to use of a sensor device 104 as a data sensing device. Sensor device 104 may be any device suitable for inspecting a structure. The present invention is not to be understood as being limited to a particular sensor device, although certain examples may make reference to particular types of sensor devices. Examples of sensor devices include, but are not limited to, cameras, infrared sensing devices, moisture sensing device, sound sensing (to listen for rodents, running water, material density, insulation gaps, etc.), gas sensing devices, material sensing devices, x-ray, thermal sensing devices, and the like.

As shown in FIGS. 1A and 1B, roof inspection system 100 includes a sensor device 104 coupled to (e.g., mounted in) adjustable sensor mount 114. Sensor device 104 may be, for example, a light weight and/or high resolution multispectral sensor. Sensor device 104 can be, for example, a remotely controllable and/or remotely operable sensor. That is, sensor device 104 can be controlled and/or operated from a location other than the location of the sensor device 104, as will be further described herein.

Sensor device 104 in one example may capture (e.g., produce, generate, and/or acquire) a number of multispectral images (e.g., a number of digital images) of a roof (e.g., roof 116) that is being inspected. For example, sensor device 104 may capture a number of images of a roof that has been damaged due to, for instance, a storm, wind, hail, falling tree(s), water, and/or fire, among other causes of damage. Sensor device 104 can capture images of a portion(s) of the roof (e.g., the damaged portion(s)) and/or images of the entire roof. As an example, after sensor device 104 captures an image of a roof, adjustable sensor mount 114 (e.g., the position of adjustable sensor mount 114) can be adjusted (e.g., moved), and sensor device 104 can then capture a different image of the roof (e.g., an image of a different portion of the roof) after adjustable sensor mount 114 is adjusted.

In some embodiments, sensor device 104 may be a releasable (e.g., detachable and/or removable camera)

device. That is, sensor device 104 can be released (e.g., detached and/or removed) from adjustable sensor mount 114. For instance, sensor device 104 can be released from adjustable sensor mount 114 after capturing an image of the roof. In such embodiments, after sensor device 104 is released from adjustable sensor mount 114, sensor device 104 may move around on the roof to capture images of different parts of the roof. Sensor device 104, in one embodiment, may include mechanical devices that may be actuated to allow it physically contact a structure as part of the inspection process. For instance, mechanically actuated devices may poke, hammer, tap, or create friction against a structure in order to collect data. In one example, such devices may work in conjunction with other devices to collect such data. For instance, a mechanical device may tap a structure and a sound sensor may listen to the sound produced by the mechanical device tapping the structure and diagnose a condition of the structure.

For example, sensor device 104 can move around on the roof to capture images of portions of the roof that may not be accessible to pole 102 (e.g., portions of the roof that may not be accessible to sensor device 104 when it is attached to the end 108 of pole 102). For instance, sensor device 104 be moved to capture an image over an edge(s) of the roof (e.g., to peak over the edge of the roof). In one embodiment, sensor device 104 may include remotely controlled mechanical components, such as wheels or coasters components that may enable sensor device 104 to traverse the roof. In one example, sensor device 104 may include propeller elements that may provide sensor device 104 with the capability to fly over the roof or structure under inspection. In another embodiment, sensor device 104 may be connected to a housing that includes components that enable it to fly over or traverse a structure.

In one embodiment, sensor device 104 may be positioned within a structure. For instance, sensor device 104 may be positioned within an attic or crawlspace through utilization of adjustable sensor mount 114 and used to inspect a crawlspace through manipulation of pole 102. In another example, sensor device 104 may be released from adjustable sensor mount 114 and used to inspect crawlspace remotely through utilization of wheels, coasters, and/or propeller elements as was described above. The multispectral capability of sensor device 104 will allow sensor device 104 to transmit information regarding the crawlspace that would allow an operator to make a determination as to whether or not there is structural damage within the crawlspace. For example, sensor device 104 may transmit images, or sensor data, showing structural degradation, hot spots, gas leaks, etc.

In another embodiment, sensor device 104 may be permanently or semi-permanently positioned within a structure and remotely operated to inspect the structure. For instance, sensor device 104 may be positioned within an attic. Sensor device 104 may then be programmed to periodic perform inspections of structure. Such inspections may occur in accordance with a schedule at regular intervals through programming of a calendar or timer. Such inspections may occur on an ad hoc basis, such as in response to an event, e.g., a weather or sound event. For example, rain or hail on a roof could be sensed by sound or by a remote weather trigger from a weather radio frequency or by the Internet. In both instances, one or more sensors may collect instantaneous, periodic, or continuous data collection depending on the event trigger (e.g., a rodent may trigger video and heavy rain may trigger two photos an hour apart). A sensor response may vary depending on other environmental variables, such as the temperature, barometric pressure, and humidity at the time of the event trigger. In one example, temperature change of an area and ambient temperature change are two variables that may cause the initiation of active observation of a leak such that the remedial focus may be on repair rather than replacement.

It should be noted that in one embodiment sensor device may inspect the roof on the exterior and the attic on the interior. The data from the inspection may then be matched such that the combined data may be used to make a three dimensional model of the inspected areas.

In one embodiment, sensor device 104 may be affixed to a structure. For instance, sensor device 104 may be suspended from a structure. Propeller elements attached to sensor device 104 may be utilized to navigate sensor device in a regular pattern through the structure. In another embodiment, sensor device 104 may be freestanding within a structure. Sensor device 104 may utilize ground propelling elements, such as wheels, coasters, or treads, to navigate through the structure.

In some embodiments, sensor device 104 can be a hotspot (e.g., a Wifi hotspot) that can create its own network (e.g., its own wireless network) (not shown in FIG. 1A or 1B). As used herein, a "network" (e.g., the network created by sensor device 104) can provide a communication system that directly or indirectly links two or more computers and/or peripheral devices (e.g., sensor device 104 and mobile device 112, as will be further described herein) and allows users to access resources on other computing devices and exchange messages with other users. A network can allow users to share resources on their own systems with other network users and to access information on centrally located systems or on systems that are located at remote locations. A network may also allow sensors to compare performance of like structures at the same time to compare performance under identical conditions.

In one embodiment, sensor device 104 may interact with one or more smart home management devices. For instance, sensor device 104 may interact with sensors that are attached to a structure (e.g. leak sensors). Sensor device 104 and the other sensors may cooperate to inspect a possible structural failure. In one example, a first type of leak sensor(s) (attached to water system) and a second type of leak sensor (leak not attached to the water system) may interact with each other and/or sensor device 104. In the event that sensors identified a possible structural failure, sensor device 104 may inspect the location of the possible failure and initiate a proactive repair such that a loss would be prevented.

A network may provide connections to the Internet and/or to the networks of other entities (e.g., organizations, institutions, etc.). Users may interact with network-enabled software applications to make a network request, such as to trigger sensors, get a file, or print on a network printer. Applications may also communicate with network management software, which can interact with network hardware to transmit information between devices on the network.

As shown in FIGS. 1A and 1B, roof inspection system 100 includes an attachment 106 coupled to pole 102 (e.g., to a shaft and/or one of the extendable sections of pole 102). In the embodiments illustrated in FIGS. 1A and 1B, attachment 106 is an extendable bipod attachment. Although the embodiments illustrated in FIGS. 1A and 1B include one attachment 106 coupled to pole 102, embodiments of the present disclosure are not so limited, and can include any number (e.g., more than one) of attachments 106 coupled to pole 102.

In some embodiments, attachment 106 may not be a releasable (e.g., detachable and/or removable) attachment. That is, attachment 106 may not be releasable from pole 102.

Attachment 106 can be used to stabilize pole 102 (e.g., prevent pole 102 from moving) while pole 102 is on the roof (e.g., while pole 102 is extended and/or while sensor device 104 is capturing images of the roof) and/or to move pole 102 along the roof. As an example, after sensor device 104 captures an image of a roof, and while pole 102 remains extended, attachment 106 can be used to move pole 102 to a different location on the roof and stabilize pole 102 at the different location. Sensor device 104 can then capture a different image of the roof (e.g., an image of a different portion of the roof) while pole 102 is stabilized at the different location. Further, attachment 106 can provide consistent distances for pole 102 that can result in sensor device 104 capturing standardized images of the roof. Attachment 106 will be further described herein (e.g., in connection with FIG. 2).

As shown in FIG. 1A, roof inspection system 100 includes a mobile device 112. Mobile device 112 can be, for example, tablet, a mobile phone, a smart phone, a personal digital assistant (PDA), a smart device, etc. Mobile device 112 can be a hotspot that can create its own network (not shown in FIG. 1).

Mobile device 112 (e.g., a user of mobile device 112) can communicate with, control, and/or operate sensor device 104 via the network created by mobile device 112 and/or the network created by sensor device 104. For example, mobile device 112 can instruct sensor device 104 to capture an image of a roof (e.g., roof 116) and send (e.g., transmit) the captured image to mobile device 112. Mobile device 112 can receive the captured image of the roof sent from sensor device 104 and/or display the captured image (e.g., to a user of mobile device 112), as will be further described herein. As an additional example, mobile device 112 can release sensor device 104 from pole 102 and move sensor device 104 around on the roof after sensor device 104 is released from pole 102.

In some embodiments, mobile device 112 can send the captured image of the roof to an additional computing device (not shown in FIG. 1A or 1B). The additional computing device can be, for example, a mobile device (e.g., a tablet, a mobile phone, a smart phone, a personal digital assistant (PDA), a smart device, etc.), a laptop computer, or a desktop computer, among other types of computing devices. The additional computing device can be located at or near the location of roof inspection system 100, or at a location remote to roof inspection 100 (e.g., at a building of the insurance company).

In the embodiment illustrated in FIG. 1A, mobile device 112 is coupled to pole 102 (e.g., near the bottom of pole 102). Mobile device 112 can be coupled to pole 102 by, for example, an adjustable (e.g., flexible) mount (not shown in FIG. 1A). However, embodiments of the present disclosure are not so limited. For example, in some embodiments, mobile device 112 may not be coupled to pole 102. Further, in some embodiments, mobile device 112 can be releasable from pole 102. For instance, in some embodiments, mobile device 112 can be coupled to a strap (e.g., a utility strap) that can be worn by (e.g., hooks around the neck of) the user (e.g., operator) of mobile device 112. Mobile device 112 will be further described herein (e.g., in connection with FIG. 3).

Roof inspection system 100 can, for example, be used by a claims adjuster of an insurance company or a technician to inspect the roof of a building (e.g., roof 116) covered by an insurance policy issued by the insurance company. For example, the claims adjuster can use roof inspection system 100 to inspect a roof that has been damaged due to, for instance, a storm, wind, hail, falling tree(s), water, and/or fire, among other causes of damage, as part of a claims process. For instance, the claims adjuster may use roof inspection system 100 to assess the condition of the roof (e.g., the extent and/or amount of the damage to the roof) in order to determine whether a loss exists and/or estimate the cost of repairing the damage.

By using roof inspection system 100 to inspect the roof, the claims adjuster can inspect the roof and other places not accessible from the ground without having to physically climb on to the roof and/or walk around on the roof. For example, the claims inspector may be able to inspect the roof from the ground. In contrast, in some previous roof inspection approaches, the claims adjuster may need to physically climb on to a roof (e.g., using a ladder) and/or walk around on the roof in order to inspect the roof. Accordingly, using roof inspection system 100 to inspect a roof can be more accurate, safer, less costly, and/or less time consuming than such previous roof inspection approaches.

Figure 2:
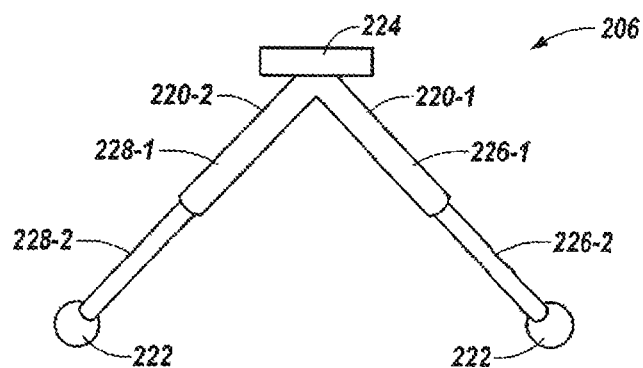
FIG. 2 illustrates an attachment of a structure inspection system in accordance with one or more embodiments of the present disclosure.

FIG. 2 illustrates an attachment 206 (e.g., an extendable bipod attachment) of a roof inspection system in accordance with one or more embodiments of the present disclosure. Attachment 206 can be, for example, attachment 106 of roof inspection system 100 previously described in connection with FIGS. 1A and 1B.

As shown in FIG. 2, attachment 206 includes members (e.g., legs) 220-1 and 220-2. Members 220-1 and 220-2 can be, for example, extendable members having a number of extendable sections (e.g., segments). For instance, in the embodiment illustrated in FIG. 2, members 220-1 and 220-2 each include two extendable sections (e.g., member 220-1 includes sections 226-1 and 226-2, and member 220-2 includes sections 228-1 and 228-2). However, embodiments of the present disclosure are not limited to a particular number of extendable sections for members 220-1 or 220-2.

Attachment 206 (e.g., one or more sections of the members of attachment 206) can be extended (e.g., partially or fully extended) while roof inspection system 100 is being used to inspect a roof (e.g., roof 116). For example, attachment 206 can be extended before extending pole 102 and/or before stabilizing pole 102 on the roof. In the embodiment illustrated in FIG. 2, attachment 206 is in a fully extended position (e.g., all sections of members 220-1 and 220-2 are extended). While extended (e.g., while in the fully extended position illustrated in FIG. 2), attachment 206 can be used to stabilize pole 102 (e.g., prevent pole 102 from moving) while pole 102 is on the roof and/or to move pole 102 along the roof.

Attachment 206 (e.g., the sections of members 220-1 and 220-2) can be retracted (e.g., not extended) when roof inspection system 100 is not in use. For example, attachment can be retracted while roof inspection system 100 is being stored and/or transported.

As shown in FIG. 2, attachment 206 includes a wheel 222 coupled to the end (e.g., the bottom) of each member 220-1 and 220-2. That is, a wheel 222 can be coupled to a part of (e.g., the end of) the last section of member 220-1 (e.g., section 226-2), and to a part of (e.g., the end of) the last section of member 220-2 (e.g., section 228-2), as illustrated in FIG. 2.

As shown in FIG. 2, attachment 206 includes a coupling member 224 coupled to members 220-1 and 220-2. Coupling member 224 can couple members 220-1 and 220-2 to a pole (e.g., pole 102 previously described in connection with FIG. 1) of the roof inspection system. Embodiments of the present disclosure are not limited to the particular coupling member 224 illustrated in FIG. 2, and can include any type of coupling member that can couple members 220-1 and 220-2 to the pole of the roof inspection system.

Figure 3:
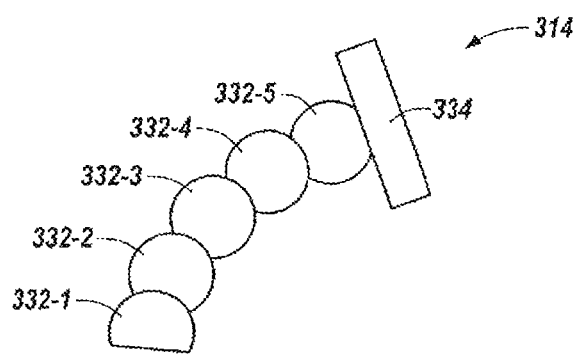
FIG. 3 illustrates an adjustable sensor mount of a structure inspection system in accordance with one or more embodiments of the present disclosure.

FIG. 3 illustrates an adjustable camera mount 314 of a roof inspection system in accordance with one or more embodiments of the present disclosure. Adjustable camera mount 314 can be, for example, adjustable sensor mount 114 of roof inspection system 100 previously described in connection with FIGS. 1A and 1B.

Adjustable camera mount 314 can include a number of flexible members. For example, adjustable camera mount 314 can include a number of flexible spherical shaped members coupled in series. For instance, in the embodiment illustrated in FIG. 3, adjustable camera mount 314 includes five flexible spherical shaped members (e.g., spherical shaped members 332-1, 332-2, 332-3, 332-4, and 332-5) coupled in series (e.g., spherical shaped member 332-2 is coupled to spherical shaped member 332-1, spherical shaped member 332-3 is coupled to spherical shaped member 332-2, spherical shaped member 332-4 is coupled to spherical shaped member 332-3, and spherical shaped member 332-5 is coupled to spherical shaped member 332-4). The first 'flexible spherical shaped member of the series (e.g., spherical shaped member 332-1) can be coupled to an end of a pole (e.g., end 108 of pole 102 previously described in connection with FIG. 1) of the roof inspection system. Embodiments of the present disclosure, however, are not limited to a particular number of flexible members or a particular type (e.g., shape) of flexible member for adjustable camera mount 314.

Adjustable camera mount 314 can include a camera mount coupled to one of the flexible members. For example, in the embodiment illustrated in FIG. 3, adjustable camera mount 314 includes a camera mount 334 coupled to the last flexible spherical shaped member of the series (e.g., spherical shaped member 332-5). A camera (e.g., sensor device 104 previously described in connection with FIG. 1) can be coupled to the camera mount.

As shown in FIG. 3, adjustable camera mount 314 (e.g., the position of adjustable camera mount 314) can be adjusted (e.g., moved and/or bent) by adjusting (e.g. moving and/or bending) one or more of the flexible members, Accordingly, adjustable camera mount 314 can provide flexibility for a camera (e.g., sensor device 104) mounted therein, while at the same time keeping the camera stable while it is in use.

Figure 4:
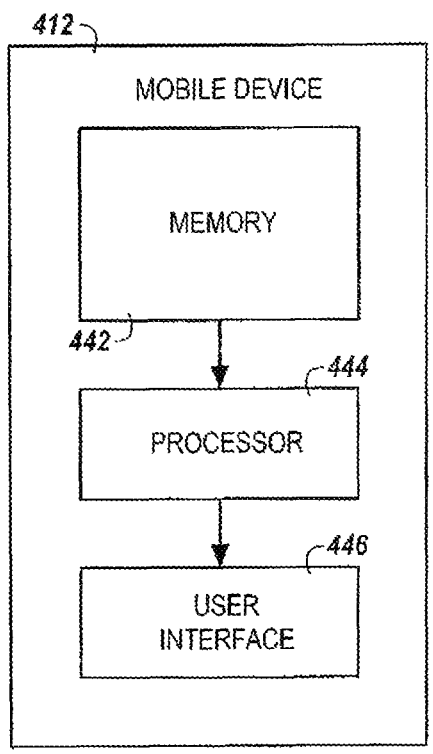
FIG. 4 illustrates a mobile device of a structure inspection system in accordance with one or more embodiments of the present disclosure.

FIG. 4 illustrates a mobile device 412 of a roof inspection system in accordance with one or more embodiments of the present disclosure. Mobile device 412 can be, for example, mobile device 112 of roof inspection system 100 previously described in connection with FIGS. 1A and 1B.

As shown in FIG. 4, mobile device 412 includes a memory 442 and a processor 444 coupled to memory 442. Memory 442 can be any type of storage medium that can be accessed by processor 444 to perform various examples of the present disclosure. For example, memory 442 can be a non-transitory computer readable medium having computer readable instructions (e.g., computer program instructions) stored thereon that are executable by processor 444 to perform various examples of the present disclosure. That is, processor 444 can execute the executable instructions stored in memory 442 to perform various examples of the present disclosure.

Memory 442 can be volatile or nonvolatile memory. Memory 442 can also be removable (e.g., portable) memory, or non-removable (e.g., internal) memory. For example, memory 442 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disk read-only memory (CD-ROM)), flash memory, a laser disk, a digital versatile disk (DVD) or other optical disk storage, and/or a magnetic medium such as magnetic cassettes, tapes, or disks, among other types of memory.

Further, although memory 442 is illustrated as being located in mobile device 412, embodiments of the present disclosure are not so limited. For example, memory 442 can also be located internal to another computing resource (e.g., enabling computer readable instructions to be downloaded over the Internet or another wired or wireless connection).

In some embodiments, memory 442 can have computer readable instructions stored thereon that are executable by processor 444 to communicate with, control, and/or operate sensor device 104 previously described in connection with FIGS. 1A and 1B. For example, memory 442 can have computer readable instructions stored thereon that are executable by processor 444 to instruct sensor device 104 to capture an image of a roof (e.g., roof 116 previously described in connection with FIG. 1B) and send (e.g., transmit) the captured image to mobile device 412. As an additional example, memory 442 can have computer readable instructions stored thereon that are executable by processor 444 to release sensor device 104 from pole 102 previously described in connection with FIGS. 1A and 1B and move sensor device 104 around on the roof after sensor device 104 is released from pole 102.

As shown in FIG. 4, mobile device 412 includes a user interface 446. User interface 446 can provide (e.g., display and/or present) and/or receive information (e.g., data and/or images) to and/or from a user (e.g., operator) of mobile device 412. For example, user interface 446 can include a screen (e.g., viewfinder) that can display images to the user of mobile device 412.

As an example, user interface 446 can display the image of the roof captured and sent to mobile device 412 by sensor device 104. In some embodiments, user interface 446 can display the image of the roof as sensor device 104 captures the image. That is, the user of mobile device 412 can view the image as it is being captured by sensor device 104 (e.g., the user can see what sensor device 104 sees).

The user of mobile device 412 can be, for instance, a claims adjuster of an insurance company who is performing an inspection of a roof, as previously described herein, or a technician trained to use the device for inspections. By viewing the image of the roof on user interface 446 of mobile device 412, the claims adjuster can inspect the roof and other places not accessible from the ground without having to physically climb on to the roof and/or walk around the roof, as previously described herein.

Figure 5:
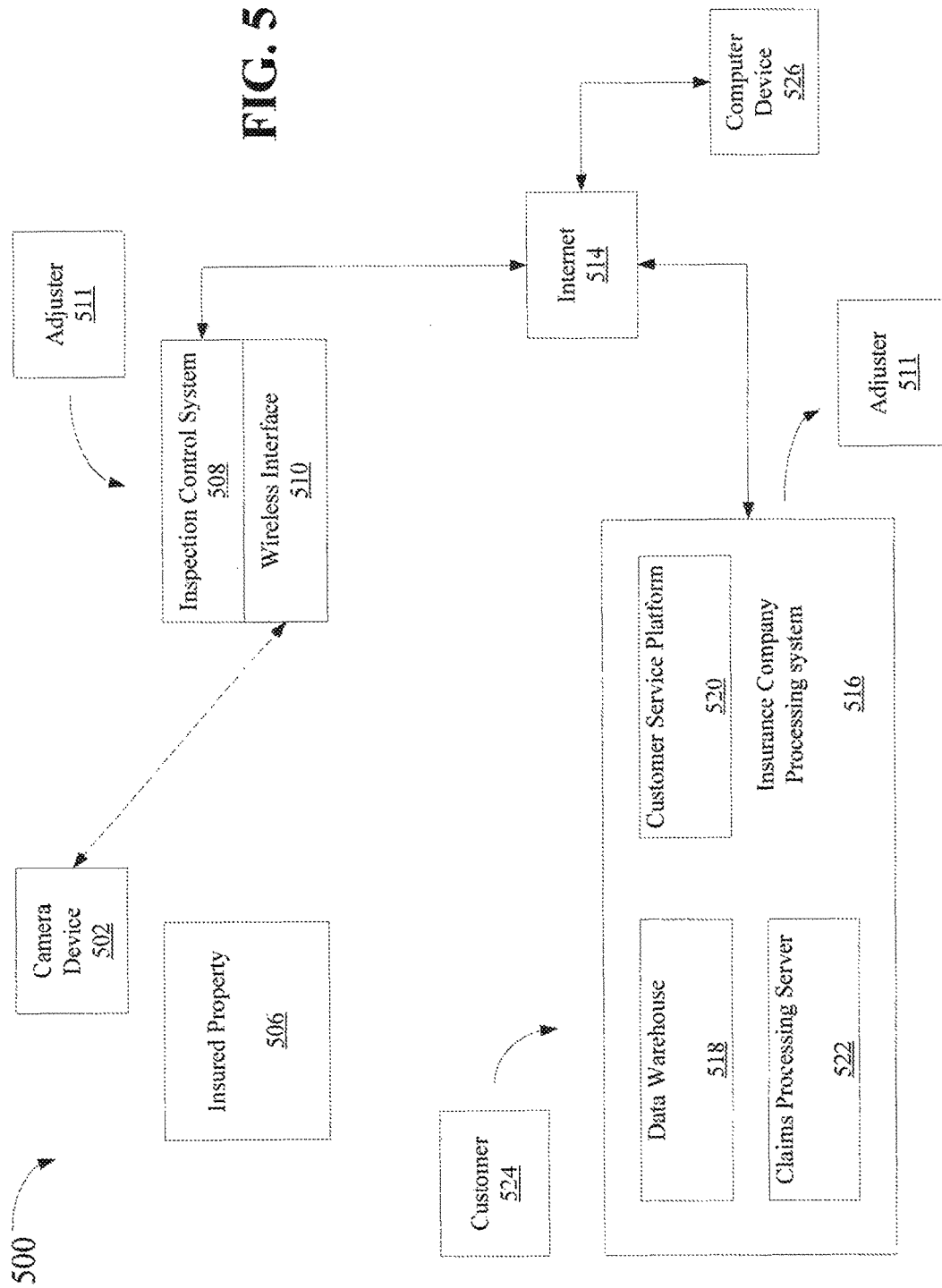
FIG. 5 illustrates a block diagram of an inspection system and an electronic claim processing system.

With reference now to FIG. 5, another embodiment is depicted which illustrates a inspection camera device 502 (such as sensor device 104) in the context of an insurance claim processing system 500. The camera device 502 is shown on the roof of a house 506 being inspected and being controlled by a remotely located inspection control system 508. The inspection control system 508 can be a computer system, such as a laptop, or handheld device (such as mobile device 112) with the appropriate software for operating the camera device 502 and the overall inspection process. The inspection control system 508 can communicate with the camera device 502 through a wireless interface 510 by wireless signals indicated by a dashed line 504 and the inspection control system 508 can also communicate with the insurance claim processing system 516 through the internet 514 or other network connection. Live or recorded video images of the inspection from the camera device 502 can be displayed on a video monitor (not shown) of the inspection control system 508. In some embodiments, the digital video signals may be stored on the computer server in the inspection control system 508. The inspection control system 508 may have an input device (e.g., keyboard, mouse, and/or joystick) controlled by an operator/adjuster 511 (or other person) for controlling images captured from the camera device 502. Alternatively, software operating on the inspection control system 508 can have a control panel or interactive graphical user interface for controlling camera device 502. Other features of the inspection control system 508 can include storage for storing the received data and a network connection (e.g., cellular wireless) to connect to the insurance claim processing system 516.

The inspection control system 508 can be connected through a computer network (e.g., the Internet) 554 to the insurance company's insurance claims processing system 516. By electronically connecting the inspection control system 508 to the claim processing system 516, inspection reports can be created and submitted electronically, improving the efficiency of the claim process. Also, annotations can be made to the recorded video or sensor data to form part or all of the inspection report. In this way, the inspection report can be easily generated, stored, and reviewed. Additionally, video and sensor data collected by the camera device 502 can also be stored along with the report. The inspection control system 508 can also be integrated with email, messaging, and scheduling systems, allowing a claim adjuster to carry a single computer with him/her for both office tasks and inspections. The inspection control system 508 or portion thereof may be incorporated into the camera device 502. In that case, the camera device 502 communicates with and may be controlled by commands over the internet from the adjuster's 511 computer 526 (which may also incorporate portions of the inspection control system 508 and/or the input device 512).

The reported and collected data can be stored in a data warehouse 518 where it can be accessed by a claim processing server 522 to make reimbursement payments to the policyholder. Further, the data can be accessed by customer service 520, or policy holders or customer 524 live in real time or at a later time, so that they can review the data collected during the inspection in detail. The database can be analyzed using data warehousing and analysis techniques, in order to better support the insurance company's business, which may preferably be performed in real time with local and/or cloud data/analysis software. For example, the data can be analyzed to determine trends and patterns in claims and damage, and this can be presented to the person reviewing this information via a computer terminal. This analysis could be assisted by a person reviewing data and video of damaged roofs or other structural portions. These trends and patterns can assist in making maintenance inspections, responding to disasters, or detecting fraud. For instance, one such use is where the system identifies the area of loss and provides the estimate. Thus, a skilled operator is not required. The system is preferably configured and operable to learn from data warehouse images and sensor data of past inspections and related estimates and actual repair costs to inform the estimate based on systematic comparison of sensor and/or inspector data inputs (such as material (image would compare attributes input as data to visually acquired data) age, orientations, and any environmental factors that would contribute to the loss probability equation).

It can also be used to better price insurance policies, adjust a policy holder's premiums, and/or adjust the claim reserves. Customers 524 can access the insurance company's processing system 516 to determine information about their property inspection. Also, the customer 524 may view the inspection images and/or data over the internet or other network in real time during the inspection or after the inspection is complete. The data and images from the inspection can also be used to help reconcile questions about the adjustor's cost estimate from the policyholder and/or contractor(s) performing the repair work. The data and images can also be helpful for remote or absentee owners or managers, such as for commercial or rental properties. The data may also be used to prevent claims by (i) providing advice or (ii) initiating a claim for the purpose of covering or sharing loss mitigation cost (iii) assisting the repair service in pinpointing problem areas that are not detectable using traditional inspection methods employed by most contractors (iv) informing macro loss mitigation strategies for similar homes with the same age, environment, and construction.

Figure 6:
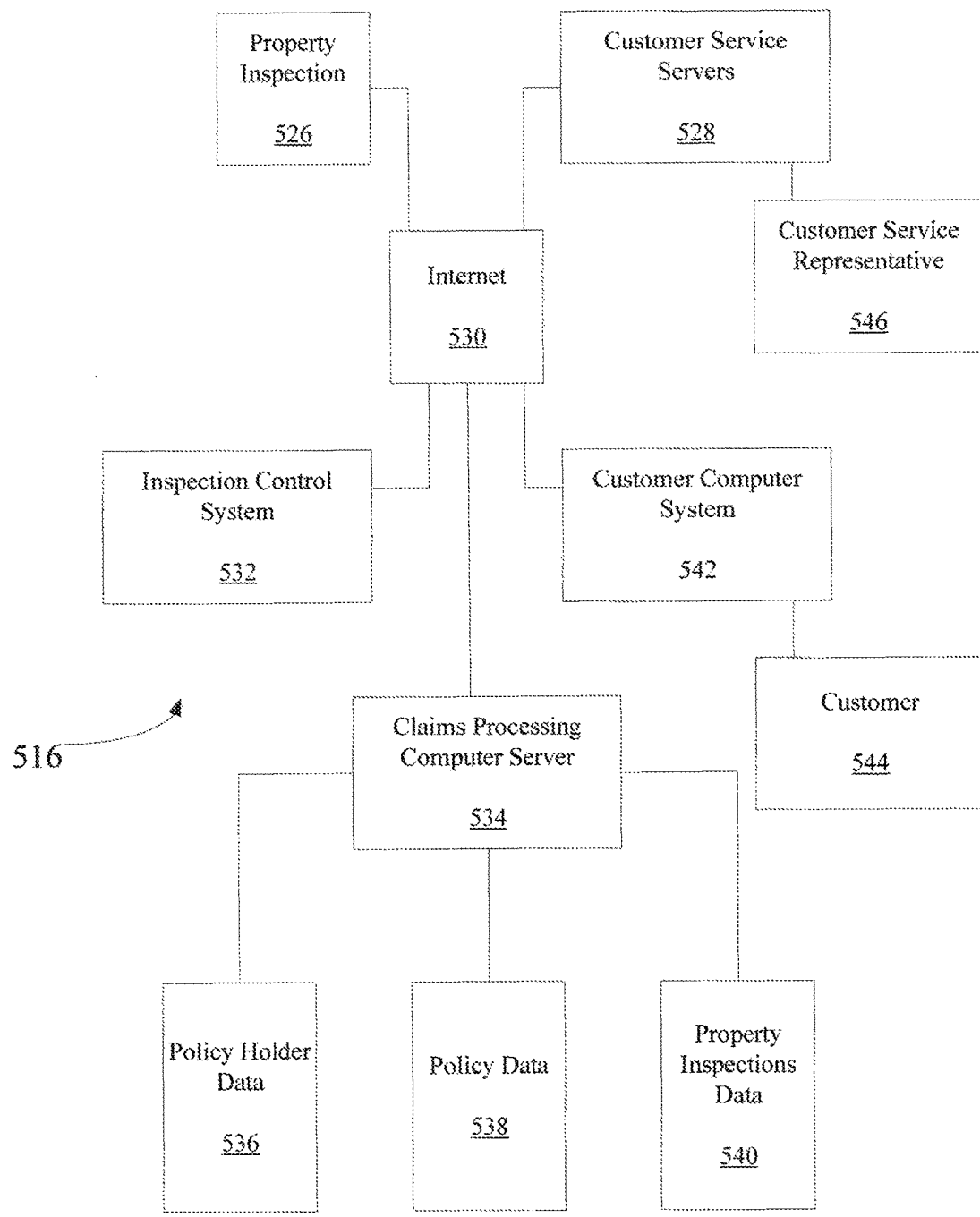
FIG. 6 illustrates further details of an electronic claim processing system.

With reference now to FIG. 6, illustrated are further details of the electronic insurance company claim processing system 516 of FIG. 5, which may be referred to as a "Central Enterprise" claim system, and how it interacts with the inspection control system 508 of FIG. 5 shown as 532 in FIG. 6. The claims processing computer server 534 coordinates data from the property inspections 526, requests from customer service representatives (or users) 546 of the insurance company customer service server 528, and customer (or policy holders or users) 544 of a customer computer system 542 which may be a PC, Laptop, smartphone, PDA, tablet device, a smart home control system, or any other computer device. The claim processing computer server 534 is connected to various databases 536-540, such as, a policy holder database 536, policy data database 538, and property inspections with sensor data database 540. The various components of the claim processing system can be connected through any type of data network, such as the Internet 530.

Customer service computer servers 528 are a set of computer systems and servers used by insurance company customer service representatives 546 to service the customers (or policy holders) 544. This can include responses to requests for information, processing customer claims, and dealing with customer payment issues. These customer service computer servers 528 are connected to the claims processing computer server 534 and the attached databases 536-540, therefore, they are able to access information and control the processing of a customer's claim or payment. In addition, the customer (or policyholder) 544 can perform certain tasks themselves using their customer computer system 542. The customers 544 can access the claims processing server 534 and databases 536-540 through the internet 530 or other network. The customer 544 can perform tasks similar to the insurance company customer server representative 546, including checking on the status of their claim or payment, and reviewing their property inspection video and data 526 electronically.

Claims processing server 534 is responsible for processing property inspection data 526 and applying the appropriate logic and rules to determine how to make a payment based on the inspection. The claims processing server 534 is connected to policy holder data database 536, which stores information about the policy holder for which a claim is being processed. The claims processing server 534 is also connected to policy data database 538 which includes information about a policy holder's policy, such as, the terms of the agreement, deductibles, coverage dates, etc. The claims processing server is also connected to a database or data warehouse storing the property inspections 540, including the recorded sensor data. This database can be used during the processing of an inspection to analyze and compare similar property inspections. These similar property inspections may be grouped by policy, geography, or type of damages.

Comparisons can be made for prospecting new customers, assessing a claim, detecting a fraudulent claim, or for underwriting, pricing, or rating new or existing customers (discussed more hereinafter). Although three separate databases are shown, additional sources of information can also be used by the claims processing server, and any of the databases could be combined into one large database, or multiple smaller databases. Further, each database can be hosted on a separate computer server, or multiple databases can be hosted on a single server. These databases provide information to the claims process server when it is processing claims along with the digital information in the property inspections, including the sensor data within the inspections (e.g., scanning of data to identify heuristics of an actual loss; such scanning can also inform the inspector/technician if the images satisfy the claim and may direct for additional sensors or image capture to be completed by specific instructions to complete analysis of the suspected loss).

Inspection control system 532 is also connected to the claims processing server 534 through the Internet 530. The inspection control system 532 can feed information directly to the claims processing server 534, and/or generate property inspection containing the same data. Further, by linking the inspection control system 532 to the customer service server 528 and customer computer system 542, both customer (or policy holder) 644 and insurance company customer service representative 564 can monitor or participate in the property inspection in real-time or at any later time.

With system 500 being described above, with reference now to FIG. 7A, an illustrated method of operation of system 500 will now be described.

Starting at step 710, an operator of camera device 502 (e.g., an insurance adjuster 511) causes it to capture one or more preferably digital images in connection with an inspection of the insured property 506, or a portion thereof (e.g., the roof portion). The one or more captured digital images are then preferably transmitted to the insurance processing system 516 (step 720). The aforesaid transmission is preferably accomplished via a wireless transmission via wireless interface 510 and a network (e.g., Internet 514). Once the one or more images are received in the insurance processing system 516, they are analyzed to determine a conduct to be followed regarding the ongoing inspection of property 506 (step 730). It is to be appreciated the aforesaid analysis of the received images and sensor data may include determining a structural integrity of material (e.g., roofing material) captured in the one or more images. The structural integrity of the material may be determined via a pixel analysis (or any form of data analysis that may be applied to images, video and sensor data collected) of the one or more captured digital images of the property 506. In one embodiment, different types of sensor data may be combined to analyze a structure. Tapping on a surface may indicate solid wood or rotten wood. A sensor collecting test data would analyze wave forms rather than pixels. Overlaid sound on the pixels may indicate termites if there were limited sound or visual data that is definitive when combined. It may be more appropriate to describe multi-spectral analysis for each collected data source by itself or combined. There are also verbal components that may assist the computer in analyzing the situation. Home owner statements may influence processing to determine likelihood of damage to be evidence under the right circumstances. E.g. when a homeowner describes a sound that would indicate damage and such damage may exist, but cannot be definitively proven with sensor data alone. Such artificial intelligence can promote the best outcome for the member and USAA without additional human intervention. The determined conduct preferably includes instructions for acquiring a certain type of image of a certain portion of property 506. For instance, the instructions may call for use of a secondary device, sensor, or camera for acquiring another data type, such as a pinging device to sense material density. The aforesaid determined conduct (instructions) is then preferably transmitted back to the operator of camera device 502 for execution thereof (step 740) (e.g., images and sensor data may be subject to software analysis to analyze the acquired information by itself or combined with other information).

With reference now to FIG. 7b, another illustrated method of operation of system 500 will now be described. With regards to capturing (step 750) and transmitting images (step 760), it is to be understood these steps are the same as above described steps 710 and 720.

At step 770, once the one or more images and related data are received in the insurance processing system 516, they are analyzed to determine a type of material (e.g., roofing material) present in the one or more captured images. The material type may be determined via a pixel analysis of the one or more captured digital images of the property 506. Also, the structural integrity of the determined material type may also be determined by system 516. The aforesaid type of material and structural integrity may be determined via a pixel analysis of the one or more captured digital images of the property 506. Next, the insurance processing system 516 preferably determines if the determined type of material is suitable for continued use on the property 502 (step 780). For instance, is the determined roof material suitable for continued use on property 506. This determination may take into consideration the geographic location of the property.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A method for performing an inspection of a structure using a remotely located multispectral sensor device comprising:

positioning a multispectral sensor within the structure, wherein the multispectral sensor includes an audio sensor and an image capture sensor;

capturing, by the multispectral sensor, data relating to a structure, the data including audio data and image data;
remotely causing the multispectral sensor to move within the structure while capturing the data;
electronically transmitting the data to a computer server and electronically receiving the data in the computer server;
analyzing the captured data in the computer server to determine a condition of the structure, wherein analyzing the data includes overlaying the audio data and the image data from a common location to determine the condition of the structure; and
electronically transmitting the condition of the structure to an operator of the multispectral sensor device.

2. The method for performing the inspection as recited in claim 1 wherein the image data and the audio data describe a roof portion of the structure.

3. The method for performing the inspection as recited in claim 1 wherein the step of remotely causing occurs in accordance with a schedule.

4. The method for performing the inspection as recited in claim 1 wherein the step of remotely causing occurs on an ad hoc basis.

5. The method for performing the inspection as recited in claim 1 wherein the multispectral sensor includes an infrared sensor.

6. The method for performing the inspection as recited in claim 1 wherein capturing, by the multispectral sensor device, data relating to the structure includes:
extending a pole having a sensor mount coupled to an end thereof;
stabilizing the extended pole on a portion of the structure using a bipod attachment coupled to the pole; and
capturing a portion of the image data or the audio data while the extended pole is stabilized on the portion of the structure using the multispectral sensor coupled to the sensor mount,
wherein positioning the multispectral sensor within the structure is accomplished using the pole, and
wherein the multispectral sensor is released from the sensor mount before moving within the structure while capturing the image data or the audio data.

7. A method for performing an inspection of an insured property using a remotely located sensor device comprising:
positioning a multispectral sensor within the insured property, wherein the multispectral sensor includes an audio sensor and an image capture sensor;
capturing, by the multispectral sensor, image data and audio data;
remotely causing the multispectral sensor to move within the insured property while capturing the image data and the audio data;
electronically transmitting the image data and audio data to a computer server located remotely from the sensor device and electronically receiving the image data and audio data in the computer server;
analyzing the image data and audio data in the computer server to determine a type and condition of material present, wherein analyzing the data includes overlaying the audio data and the image data from a common location to determine the type and condition; and
determine in the computer server if the determined type of material is suitable for continued use on the insured property based on the condition.

8. The method for performing the inspection as recited in claim 7 wherein the condition includes structural integrity of the determined type of material.

9. The method for performing the inspection as recited in claim 8 wherein the condition includes suitability of use for the determined type of material in reference to a geographic location the insured property is located.

10. The method for performing the inspection as recited in claim 7 wherein the image data and audio data are of a roof portion of the insured property.

11. The method for performing the inspection as recited in claim 7 wherein capturing by a sensor device the captured image of the insured property includes:
extending a pole having a sensor mount coupled to an end thereof;
stabilizing the extended pole on a portion of the insured property using a bipod attachment coupled to the pole; and
capturing a portion of the image data or the audio data while the extended pole is stabilized on the portion of the insured property using the sensor device coupled to the sensor mount,
wherein positioning the multispectral sensor within the insured property is accomplished using the pole, and
wherein the multispectral sensor is released from the sensor mount before moving within the insured property while capturing the data.

12. An inspection system, comprising:
an extendable pole;
an adjustable sensor mount coupled to an end of the extendable pole;
a releasable sensor device coupled to the adjustable sensor mount;
an extendable bipod attachment coupled to the extendable pole and configured to stabilize within a structure; and
a mobile device configured to instruct the releasable sensor device to:
release the releasable sensor device from the adjustable sensor mount;
capture image data and audio data of the structure;
remotely cause the sensor device to move within the structure while capturing the image data and audio data; and
send the image data and audio data to the mobile device wherein the mobile device electronically transmits the data; and
a computer server located remotely from the mobile device configured to electronically receiving the image data and audio data from the mobile device and analyze the image data and audio data to perform an inspection process of the structure, wherein analyzing the data includes overlaying the audio data and the image data from a common location to determine a condition of the structure.

13. An inspection system as recited in claim 12 wherein the computer server is further configured to electronically transmit instructions to an operator of the releasable sensor device regarding an action based on the inspection of a roof of the structure.

14. The inspection system of claim 13, wherein analyzing the image data and audio data in the computer server determines structural integrity of material at the common location.

15. The inspection system of claim 14, wherein the structural integrity of the material is determined by the computer server.

16. The inspection system of claim 13, wherein the action includes instructions for acquiring additional multispectral imagery of the structure.

17. The inspection system of claim 12, wherein the releasable sensor device includes one or more of wheels or a propeller configured to move the sensor device within the structure.

18. The inspection system of claim 12, further comprising:
a fiber optic visual sensor extendable from the extendable pole, wherein the fiber optic visual sensor collects at least a portion of the image data.

19. The method of claim 1, wherein the multispectral sensor further includes a mechanical testing device that hammers or creates friction with the structure.

20. The method of claim 1, wherein the audio sensor includes a stethoscope.

* * * * *